United States Patent
Hammond et al.

[11] Patent Number: 5,969,813
[45] Date of Patent: Oct. 19, 1999

[54] VIAL AUTOSAMPLER

[75] Inventors: Stephen V. Hammond; Tony G. Axon, both of Sandwich, United Kingdom

[73] Assignee: Pfizer Inc., New York, N.Y.

[21] Appl. No.: 08/857,922

[22] Filed: Feb. 12, 1998

[30] Foreign Application Priority Data

Apr. 17, 1997 [EP] European Pat. Off. .............. 97302641

[51] Int. Cl.$^6$ .................... G01J 3/02; G01J 3/42
[52] U.S. Cl. ............. 356/319; 356/326; 250/339.11
[58] Field of Search .................. 356/319, 326, 356/328, 446; 250/339.11, 339.12, 341.8, 340

[56] References Cited

U.S. PATENT DOCUMENTS

| | | | |
|---|---|---|---|
| 3,322,958 | 5/1967 | Heiss | 250/218 |
| 4,045,179 | 8/1977 | Bunce . | |
| 4,315,891 | 2/1982 | Sakurada . | |
| 4,346,056 | 8/1982 | Sakurada . | |
| 4,430,299 | 2/1984 | Horne | 422/64 |
| 4,540,549 | 9/1985 | Manabe . | |
| 4,668,617 | 5/1987 | Furuta et al. . | |
| 4,912,318 | 3/1990 | Kajiura et al. | 250/223 B |
| 4,933,147 | 6/1990 | Hollar et al. . | |
| 5,037,613 | 8/1991 | Shaw et al. | 422/64 |
| 5,089,229 | 2/1992 | Heidt et al. | 422/64 |
| 5,192,505 | 3/1993 | Sakagami . | |
| 5,250,262 | 10/1993 | Heidt et al. | 422/64 |
| 5,336,467 | 8/1994 | Heidt | 422/64 |
| 5,504,332 | 4/1996 | Richmond et al. | 250/339.12 |

FOREIGN PATENT DOCUMENTS 1540128  2/1979  United Kingdom .

*Primary Examiner*—F. L. Evans
*Attorney, Agent, or Firm*—Peter C. Richardson; Gregg C. Benson; Jennifer A. Kispert

[57] ABSTRACT

Apparatus for spectrophotometric analysis of material in vials 16 in which material in each vial is subjected to a beam 4 at a scanning station 20. An array of the vials 16 is carried by a carousel 60 for each vial 16 automatically and sequentially to be delivered to the scanning station and thereafter removed following scanning by the beam 4. Rotation of the carousel 60 to feed the vials to the scanning station and to remove them from that station is controlled by a computer 3 which also controls spectrophotometric measurement of the material in the respective vials whilst at the scanning station.

20 Claims, 3 Drawing Sheets

VIAL AUTOSAMPLER

TECHNICAL FIELD & BACKGROUND ART

The present invention relates to spectrophotometric analysis and is particularly concerned with apparatus for analysis of a sample material, typically in powder or liquid form, by reflectance measurements resulting from a beam of electromagnetic radiation (usually near infrared) applied to the material.

Spectrophotometers are well known to provide quantitive and qualitative analysis of substances and materials and are used extensively within the chemical, petrochemical, food, agriculture and pharmaceutical industries. Typical infrared reflectance spectrophotometers are sold under the Trade Marks "COMPSCAN" by the Gardner Neotec Division of Pacific Scientific and "MODEL 6500" by NIR Systems Inc. Generally known spectrophotometers comprise a cell or container within which a sample of the material for analysis is retained; a source providing a beam of electromagnetic radiation (usually near infrared as previously mentioned) which is applied to the material in the cell, and sensors or detectors which are responsive to reflections from the material in the cell and provide an output from which the analysis is effected. Usually the spectrophotometer is coupled to a computer by which the application of the beam to the material is controlled and which provides a required analysis of the output from the sensors or detectors.

It is an object of the present invention to provide an apparatus for spectrophotometric analysis which is an improvement over known such apparatus in so far as it facilitates effecting individual analysis measurements on sample materials in a plurality of containers.

STATEMENT OF INVENTION AND ADVANTAGES

According to the present invention there is provided apparatus for spectrophotometric analysis of a material by reflectance measurements resulting from a beam of electromagnetic radiation applied to the material which comprises a station at which a container housing the material is to be located for said measurements and means for carrying an array of said containers and feeding each container successively to locate it at said station for spectrophotometric measurements and removing the respective container from the station following said measurement; said means for carrying, feeding and removing the array of containers comprising an endless conveyor, intermittent displacement of which feeds each container successively to the station, retains the respective container stationary at the station for spectrophotometric measurement and displaces to remove the respective container from the station following measurement; and wherein the station comprises a seating to which a said container is fed to be accommodated and retained in a predetermined position for said measurement, said seating coinciding with an aperture in a plate that is opaque and substantially non-reflective to the electromagnetic radiation and through which aperture the beam is applied to the material and the reflectance measurements are detected.

Usually the electromagnetic beam will be visible light or near infrared light and for convenience the latter will hereinafter be referred to.

Conventional spectrophotometers have a scanning station at which a container of the sample material is located for analysis measurements of that material to be effected. Typically the location of the container at the station is done by a laboratory technician who subsequently carries out the analysis measurements prior to removing the container from the station. Where analysis measurements are required on sample material (or materials) in a large number or batch of containers (as is frequently required in the pharmaceutical industry) the above described typical operating procedure can present problems by becoming monotonous (and thereby susceptible to error) and by being slow and labour intensive (and thereby a relatively costly exercise). These problems can be alleviated by the apparatus of the present invention.

Desirably the feed to, and removal of the containers from, the station at which the measurements are taken is effected automatically under computer control, such computer conveniently also being programmed to effect the required spectrophotometric measurements. The means for carrying, feeding and removing the array of containers to/from the station is in the form of an endless or continuous conveyor, preferably a carousel, intermittent displacement of which feeds each container successively to the station, retains the respective container stationary at the station for spectrophotometric measurement of its sample contents and following such measurement displaces to remove the respective container from the station.

The station at which each container of sample material is to be located preferably comprises a seating to which a said container is fed to be accommodated and retained in a predetermined position for analysis measurements to be effected on the sample material. The seating for the container is conveniently provided in a plate having an aperture through which the beam is applied to the material.

Conventional spectrophotometers present the light beam on to the sample material for analysis by way of a sheet material window (typically a sheet of optical quartz) which is translucent to the beam and light reflected (in the case of reflectance spectrophotometers) from the sample is redirected through the window to the sensors or detectors (signals from which provide an output for the analysis measurements). With such apparatus it is preferred that the window is disposed between the aforementioned apertured plate and the source of the near infrared light.

The apparatus of the present invention is also provided in combination with an array of containers or cells within which samples of the material for analysis are accommodated (such samples may be of the same or different material). The container is preferably located at the seating of the station for the sample material to overlie the above mentioned aperture in the plate and to extend beyond the whole periphery of that aperture. The apertured plate can consequently serve to prevent the light beam which is directed through its aperture from being applied directly to peripheral parts of the container (which could otherwise develop spurious light reflections and adversely affect the accuracy of the spectrophotometric readings). Usually the container will have a substantially flat wall part which fully overlies the aperture and extends beyond the whole periphery of that aperture and through which wall part the light beam is directed to the sample material which extends over the wall part. The aforementioned wall part of the container is conveniently arranged to abut the apertured plate to overlie the aperture therein. In fact, where the spectrophotometer includes a window as aforementioned, the apertured plate conveniently serves to protect the window from being damaged by the container (for example by preventing the successive containers in the array from scratching the surface of the window). The previously mentioned seating for a container when located at the station will usually be sized and profiled to accommodate a predetermined size and shape of container preferably to locate and retain that container in a predetermined position over the aperture of the aforementioned apertured plate. A preferred form of container is a conventional vial as typically used for housing pharmaceutical samples and having a substantially circular flat base and a substantially cylindrical side wall extending concentrically from the base; usually the light beam and, in the case of reflectance spectrophotometry, reflected light will be directed to and from the sample material in the vial through the flat base. Preferably a vial from the array of such containers will be located in a seating or otherwise at the station to ensure that its base fully overlies the aperture of the plate whilst the whole periphery of the base (comprising its junction with the cylindrical side wall) is located wholly outside the periphery of the aperture so that the light beam is applied to illuminate the sample material in the vial through the vial base at a position other than through the vial base at its junction with the side wall. The aperture in the plate can consequently serve to define or isolate for the light beam a predetermined target area on the base of the vial remote from the peripheral junction of the base with the vial side wall and over which target area the sample material is dispersed to be subjected to the light beam. It has been determined that should the light beam be applied through the aperture of the plate to illuminate the base of the vial at its peripheral junction with the vial side wall, spurious light reflections and refractions can develop which adversely affect the accuracy of the spectrophotometric readings.

It is preferred that the light beam is directed substantially vertically. The reason for this preference is that when the sample material for analysis is a powder, it permits the powder to be uniformly dispersed over a substantially horizontal wall of the container in which it is housed in the array and through which horizontal wall the vertical light beam is applied to the material when a particular container is located at the station. It will be appreciated however that the present invention may be applied to spectrophotometers in which the light beam is directed other than vertically.

It is to be realised that the apparatus of the present invention may be utilised for analysis of sample material in a form other than powder.

DRAWINGS

One embodiment of apparatus for spectrophotometric analysis constructed in accordance with the present invention will now be described, by way of example only, with reference to the accompanying illustrative drawings in which:

FIG. 1 diagrammatically illustrates a side elevation of the apparatus for use in the analysis of material samples retained in an array of vials that are fed to the scanning station;

FIG. 2 diagrammatically illustrates a plan view of the apparatus in FIG. 1 and particularly shows a carousel by which the vials are fed to the scanning station;

FIG. 3 is an enlarged side view of part of the apparatus shown in FIG. 1 and illustrates the manner in which each vial of the array is presented at the scanning station for analysis of its contents, and FIG. 4 is a similar view to that of FIG. 3 and shows a modified form of carousel conveyor.

DETAILED DESCRIPTION OF DRAWINGS

Figure 2:
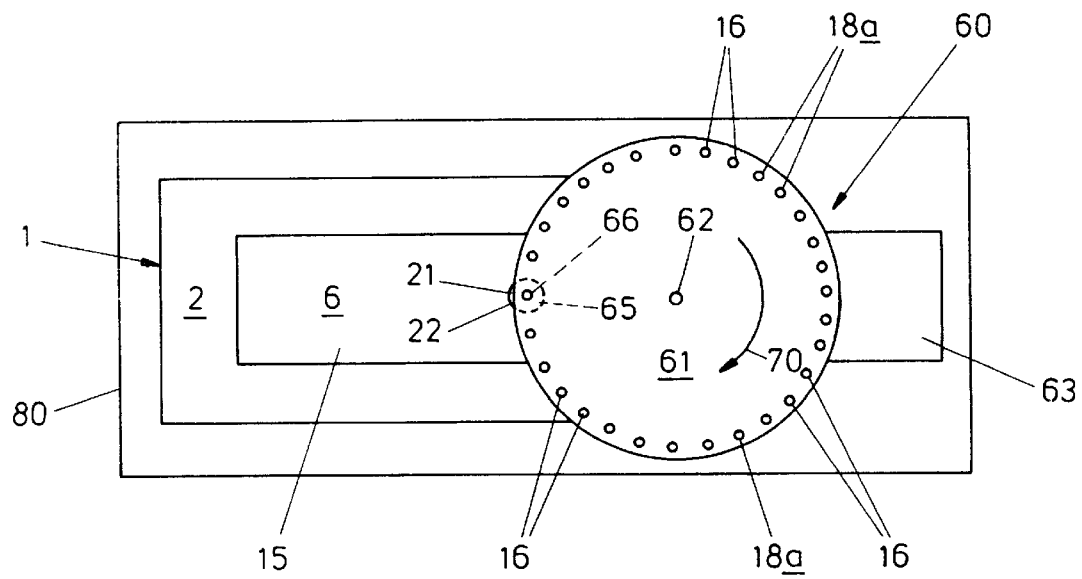

The apparatus includes a spectrophotometer unit 1 for analysis of a sample material by reflectance measurements from a beam of near infrared light that is applied to the sample. The unit 1 is, conveniently, predominantly comprised of a generally known spectrophotometer unit, for example that as sold under the Trade Mark MODEL 6500 by NIR Systems Inc. Such a known spectrophotometer has a monochromator part 2 which is usually coupled to a computer 3 (not normally regarded as part of the spectrophotometer) from which it receives commands and transmits data back for analysis purposes. The function of the monochromator 2 is well known in the art and includes a generator 4a providing monochromatic near infrared light 4 which it presents through a slit 5. Coupled to the monochromator 2 and forming part of the spectrophotometer is a reflectance module 6 into which the near infrared light 4 is presented from the slit 5. Conventionally included in the module 6 are sensors or detectors 7 which are responsive to near infrared light and when subjected to such light transmit signals to the monochromator 2 and therethrough data to the computer 3 for analysis measurements to be effected. Light 4 from the slit 5 is directed as a beam through a flat quartz sheet window 8 in a base plate 15 of the module 6 onto a sample material for spectrophotometric analysis located at a scanning station 20. The plate 15 is opaque and non-reflective to near infrared light. This sample material is housed in a vial 16 which is located adjacent to the window 8 externally of the module 6 so that light reflected from the sample material re-enters the module 6 through the window 8 to be picked up by the detectors 7 for effecting the analysis.

The apparatus shown is primarily intended for spectrophotometric analysis of pharmaceutical samples where a sample may be available only in a small quantity. Such samples P in powder form are housed within conventional pharmaceutical thin walled glass vials 16 each having a flat circular base 17 and an open topped cylindrical side wall 18 upstanding from the base to be concentric therewith and closed by a cap or stopper 18a. A vial 16 is located at the scanning station 20 on the module 6 so that its circular base 17 fully overlies a circular aperture 13 in the plate 15 which aperture is bridged by the window 8. For the purpose of locating a vial 16 correctly for analysis measurements its base stands on the plate 15 slidably accommodated in a complementary annular seating 21 presented on the base plate 15 adjacent to its aperture 13. From FIG. 3 it will be seen that the diameter of the aperture 13 is considerably less than the diameter of the vial base 17 and is also less than the internal diameter of the vial at its base 17. Consequently when the vial base 17 is located on the seating 21 to be concentric with the aperture 13, the marginal periphery of the vial base which includes the junction between that base and the side wall 18 (which junction is illustrated at 23 in FIGS. 3 and 4) does not overlie the aperture 13 and is therefore remote from the incident beam 4. A conventional pharmaceutical vial will have a base diameter not greater than 20 millimeters and a thickness for its cylindrical wall not greater than 2 millimeters, typically the vial base diameter will be 15 millimeters, the cylindrical wall thickness will be 0.5 millimeters and the vial will have a capacity in the order of 4.0 ccs. With such a typical vial the aperture 13 may have a diameter of, say, 12 millimeters.

The beam 4 is directed substantially vertically and the plate 15 is disposed in a horizontal plane. A vial 16 located at the station 20 with its base 17 horizontal and standing on the plate 15 in the seating 21 will have its sample powder P dispersed uniformly on the vial base 17 to extend fully over and beyond the whole periphery of the aperture 13. As a consequence the beam 4 directed through the aperture 13 will be applied to the powder P for light 25 reflected therefrom to be applied to the detectors 7 for spectrophotometric analysis in conventional manner. In particular, it will be noted that the periphery of the vial base which includes the junction 23 between that base and the cylindrical side wall 18 is covered by the base plate 15 to the extent that the base plate prevents light from being applied directly to the junction 23 from the beam 4. This alleviates spurious or stray light reflections which could otherwise emanate from the wall/base junction 23 of the vial from adversely affecting the accuracy of the spectrophotometric measurements.

The annular seating 21 is conveniently defined on the base plate 15 by an annular seating plate 22 located in an annular recess 22a in the plate 15. It will be appreciated that different seating plates 22 can be applied to the plate 15 (such different seating plates having different diameter seatings 21 for accommodating and locating differently sized vials 16). Also by having the seating plate 22 removable, a reference standard material (for example "Spectralon"—Trade Mark) may be fitted directly over the aperture 13 for the purpose of providing a standard approximately 99% reflective surface to the near infrared light from the beam 4 in setting up the spectrophotometer prior to carrying out an analysis measurement. The seating plate 22 presents a substantially frusto conical guide surface 22b which is concentric with the aperture 13 and converges to the seating 21. The guide surface 22b provides a lead-in over which a vial may slide to assist in location of the base 17 of the vial concentrically on the seating 21.

Figure 3:
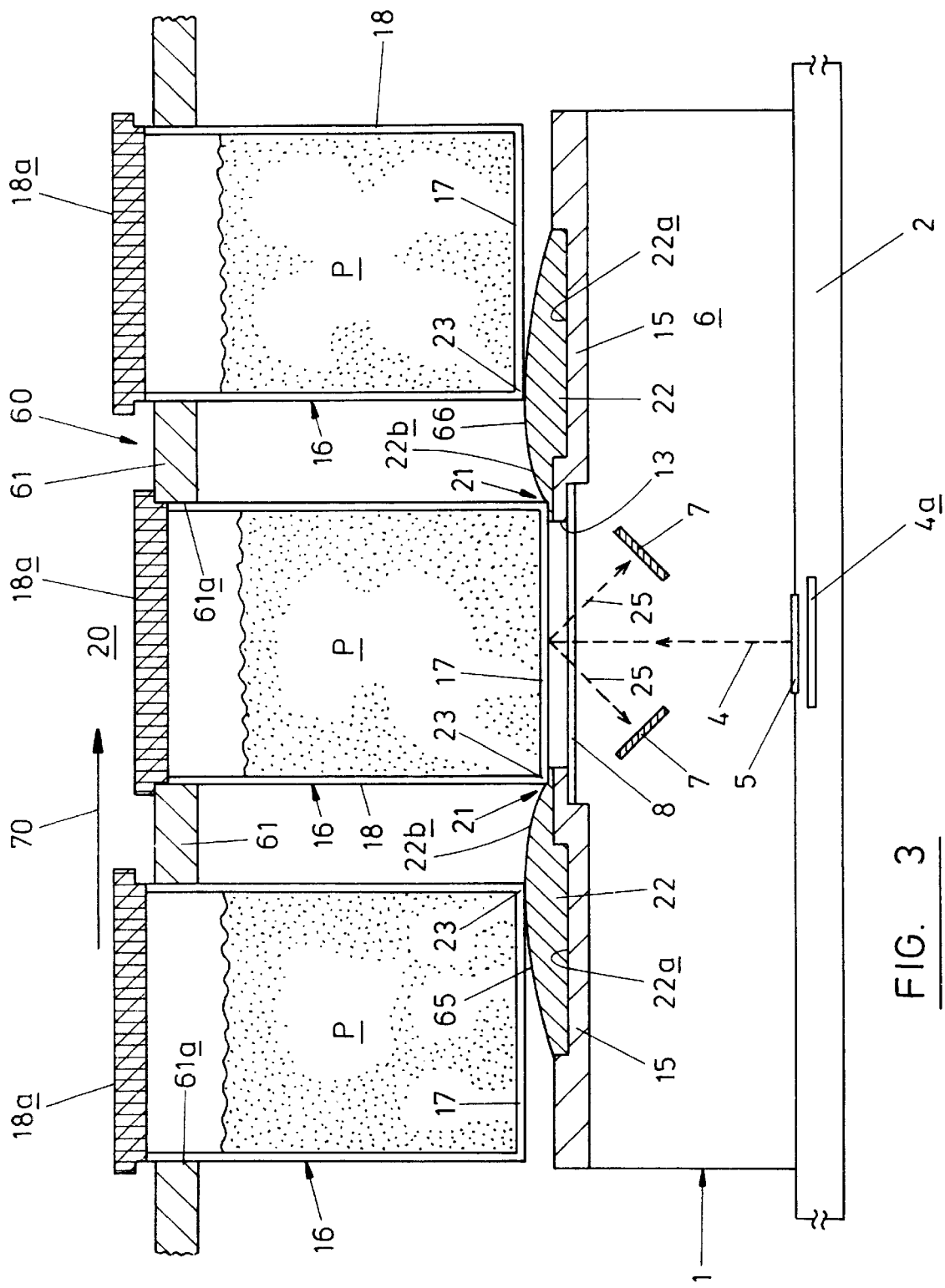

It will be seen from FIG. 3 that the base 17 of a vial 16 in the seating 21 at the station 20 stands on and is in face-to-face contact with the base plate 15 so that the beam 4 immediately enters the base of the vial from the aperture 13. Furthermore, the base plate 15 (which will usually be formed of metal) serves to protect the outer surface of the window 8 from being damaged, for example scratched, by contact with the vial base.

Vials 16 from an array thereof and each containing sample material P are fed successively and automatically to the scanning station 20 for spectrophotometric analysis of the respective samples and removed from the station following such measurement. For this purpose the apparatus includes an endless conveyor which, in the present example, is in the form of a carousel 60 comprising a substantially horizontal circular disc 61 centrally mounted for rotation on a vertical shaft 62 which is coupled to be rotated by a drive unit 63.

Figure 1:
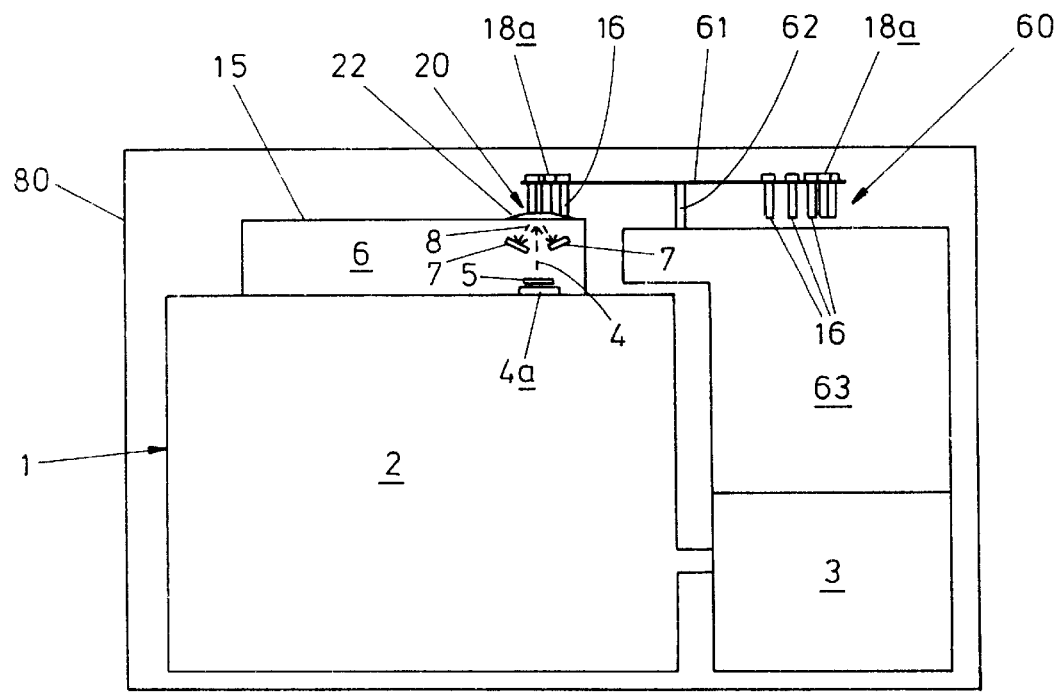

The vials 16 containing the samples for analysis are disposed in a circumferentially spaced array at the marginal peripheral edge part of the disc 61 (as best seen in FIG. 2). Each vial is received as a free sliding fit in an aperture 61a in the disc 16 and is suspended from the disc by abutment of its cap 18a with the upper surface of the disc. For convenience not all of the suspended vials 16 have been shown in FIG. 1. The drive unit 63 is controlled automatically by the computer 3 in synchronisation with actuation of the spectrophotometer 1 to rotate the shaft 62 and thereby index the disc 61 intermittently to feed the vials 16 successively to the annular vial seating 21 on the plate 15. In the embodiment shown in FIG. 3 the seating 21 is disposed between ramps 65 and 66 presented by upper substantially diametrically opposed convex surface parts on the annular seating plate 22 carried by the base plate 15. The ramps 65 and 66 are located beneath the circular path along which the vials are carried by the rotating carousel and lead and trail respectively relative to the direction of movement of the vials during rotation of the disc 61 (in the direction of arrow 70). The ramps 65 and 66 are conveniently coated with a low friction material (such as polytetrafluoroethylene) and are arranged together with the vials on the carousel so that as the disc 61 is rotated, the base 17 of a vial approaching the station 20 will abut and slide over the leading ramp 65 causing that vial to be displaced vertically upwardly relative to the disc 61 so that it is no longer suspended by its cap 18a from that disc. Further rotation of the carousel displaces the vial from the leading ramp 65 and down the frusto conical guide surface 22b to the seating 21 so that the vial is displaced downwardly under gravity to stand on the plate 15 in the seating 21 which determines the location of the vial base 17 concentric with the aperture 13. In this condition of the vial and with the carousel stationary, the spectrophotometer is actuated by the computer control to effect the analysis measurements. Following such measurements the disc 61 is further rotated to urge the vial 16 on the seating 21 into abutment with the guide surface 22b leading to the trailing ramp 66. The surface 22b to the ramp 66 causes the vial to be raised from the seating 21 and as the vial slides over that ramp clear of the station 20, it eventually drops relative to the disc 61 to be suspended therefrom by its cap 18a. The automatic intermittent rotation of the disc 61 under control of the computer 3 ensures that the feed or indexing of the vials 16 to the seating 21 is synchronised with the analysis measurements which are effected on the vial that is stationary on the seating 21.

Figure 4:
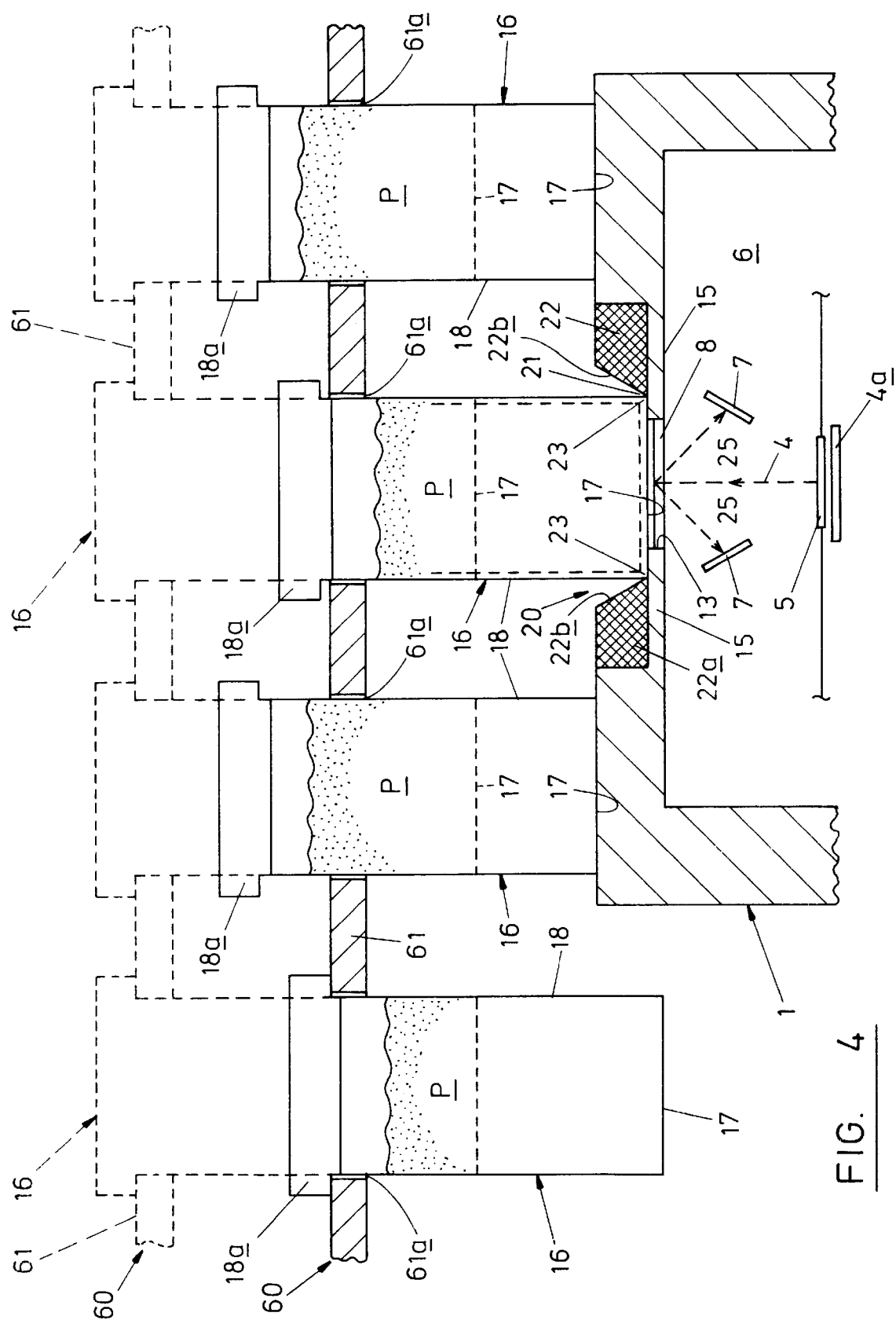

In the modification shown in FIG. 4 the disc 61 of the carousel 60 rotates about its vertical axis to index the suspended vials 16 in a relatively high plane (as indicated by the broken lines in the Figure). When a particular vial has been indexed to a position in which it directly overlies the seating 21, the disc 61 is displaced vertically downwardly along its axis of rotation to a low plane to deposit that particular vial 16 on the seating 21 (as indicated by the full lines in FIG. 4). As the disc 61 is lowered for the vial 16 to stand directly on the plate 15 in the seating 21, the cap of that vial may be moved clear of the disc 61 (by the vial's abutment with the plate 15) whilst the vial remains retained in the aperture 61a so that the vial stands alone on the seating, possibly being centralised on the seating 21 by the frusto conical guide surface 22b. It will be seen from FIG. 4 that during lowering of the disc 61, the two vials 16 which are adjacent to and on each side of the vial 16 that is in the seating 21 abut the unit 1 to be raised relative to the disc 61 but this is incidental. With the disc 61 in the low plane and the carousel stationary, the spectrophotometer is actuated by the computer control to effect the analysis measurements of the powder in the vial on the seating. Thereafter the disc 61 is raised to its high plane, again to suspend therefrom all of the vials 16 which it carries so that they are clear of the unit 1 and the disc 61 can then be rotatably indexed to locate a further vial 16 over the seating 21.

The drive unit 63 for rotatably indexing the vials 16 on the carousel will typically have an electrical stepper motor controlled by optical switches which determine the desired stop motion positions to locate a selected vial over the seating 21 under computer control. In the modification of FIG. 4, vertical displacement of the rotation shaft 62 for the disc 61 to move the disc between its high and low planes whilst indexing is conveniently effected by a further electrical drive motor controlled by limit switches.

Desirably the station 20 together with the carousel and vials 16 carried thereby are enclosed within an opaque cover 80.

We claim:

1. Apparatus for spectrophotometric analysis of a material by reflectance measurements resulting from a beam of electromagnetic radiation applied to the material which comprises a station at which a container housing the material is to be located for said measurements and means for carrying an array of said containers and feeding each of said containers successively to locate said container at said station for said measurement and removing said container from said station following said measurement, said means for carrying, feeding and removing said array of said containers comprising an endless conveyor, where intermittent displacement of said conveyor feeds each of said containers successively to said station, retains said container stationary at said station for said measurement and displaces to remove said container from said station following said measurement, said station comprising a seating to which said container is fed to be accommodated and retained in a predetermined position for said measurement, said seating being carried by a plate having an aperture through which said beam is applied to said material and said measurements are detected, said plate being opaque and substantially non-reflective to said electromagnetic radiation, said seating coinciding with said aperture, and a guide surface associated with said seating and with which said container on said conveyor may abut, said guide surface serving to provide a lead-in for said container as said container is fed to said seating to assist in location of said container at said seating.

2. Apparatus as claimed in claim 1 wherein a sheet material window translucent to said beam is disposed between said seating and a source for said beam, where said source directs said beam through said window to said material housed in said container.

3. Apparatus as claimed in claim 1 wherein said feed and said removal of said containers is controlled automatically by a computer programmed to effect said measurements.

4. Apparatus as claimed in claim 1 wherein said conveyor comprises a carousel intermittently rotatable to effect said displacement.

5. Apparatus as claimed in claim 4 wherein said intermittent rotation is about an upstanding axis, and said carousel is indexible for locating said predetermined container over said seating and is displaceable in the direction of its axis of rotation to lower said predetermined container onto said seating for said measurement and to raise said predetermined container from said seating for further indexing of said containers.

6. Apparatus as claimed in claim 4 wherein said carousel comprises a rotatable disc from which said containers are to be suspended to be carried thereby in said array spaced about the periphery of said disc.

7. Apparatus as claimed in claim 1 further comprising an opaque cover enclosing said station together with said means for carrying said array of said containers and said containers when carried thereby.

8. Apparatus as claimed in claim 1 in combination with said array of said containers, where each of said containers accommodates said material for said analysis.

9. Apparatus as claimed in claim 8 wherein said means locates said container at said station for said material in said container to fully overlie said aperture in said plate and extend beyond the periphery of said aperture.

10. Apparatus as claimed in claim 9 wherein said container has a substantially flat wall part which fully overlies said aperture and extends beyond said periphery of said aperture and through which said wall part said beam is directed to said material dispersed over said wall part.

11. Apparatus as claimed in claim 10 wherein said wall part is in abutment with said plate to overlie said aperture of said plate.

12. Apparatus as claimed in claim 11 wherein a sheet material window translucent to said beam is disposed between said seating and a source for said beam, where said source directs said beam through said window to said material housed in said container at said station and wherein said plate protects said window from abutment by said container.

13. Apparatus as claimed in claim 8 wherein each of said containers of said array is a vial having a substantially circular flat base and a substantially cylindrical side wall extending concentrically from said circular flat base and said beam is directed to said material in said vial through said circular flat base.

14. Apparatus as claimed in claim 13 wherein said seating is circular for said circular flat base to be received thereby as a substantially complementary fit.

15. Apparatus as claimed in claim 13 wherein said circular flat base accommodated by said seating fully overlies said aperture of said plate so that the periphery of said circular flat base comprising its junction with said cylindrical side wall is located wholly outside the periphery of said aperture of said plate and said beam is applied to said material in said vial through said circular flat base other than at a position through said circular flat base at its junction with said cylindrical side wall.

16. Apparatus as claimed in claim 13 wherein said vial has a base diameter not greater than 20 millimeters and a wall thickness not greater than 2 millimeters.

17. Apparatus as claimed in claim 13 wherein said circular flat base accommodated by said seating is substantially concentric with said aperture in said plate.

18. Apparatus as claimed in claim 13 wherein said guide surface is substantially frusto conical to converge to said seating and provide a lead-in for said circular flat base to said seating.

19. Apparatus as claimed in claim 1 wherein said beam is directed substantially vertically.

20. Apparatus as claimed in claim 19 wherein said station is directed upwardly and said containers are carried by said conveyor over said station and each of said containers is controlled to be deposited downwardly onto said station for said measurements and raised from said station subsequent to said measurements.

* * * * *